(12) United States Patent
Knapp

(10) Patent No.: US 9,194,040 B2
(45) Date of Patent: Nov. 24, 2015

(54) METHODS FOR PRODUCING NICKEL-CONTAINING FILMS

(75) Inventor: David Knapp, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 446 days.

(21) Appl. No.: 13/557,348

(22) Filed: Jul. 25, 2012

(65) Prior Publication Data

US 2014/0030436 A1    Jan. 30, 2014

(51) Int. Cl.
C23C 16/00 (2006.01)
C07F 15/00 (2006.01)
C23C 16/18 (2006.01)
C07F 15/04 (2006.01)

(52) U.S. Cl.
CPC *C23C 16/18* (2013.01); *C07F 15/04* (2013.01)

(58) Field of Classification Search
None
See application file for complete search history.

(56) References Cited

U.S. PATENT DOCUMENTS

| 5,352,488 | A * | 10/1994 | Spencer et al. ............ 427/250 |
| 5,387,315 | A | 2/1995 | Sandhu |
| 6,359,159 | B1 | 3/2002 | Welch et al. |
| 6,998,153 | B2 | 2/2006 | Chiang et al. |
| 7,951,711 | B2 | 5/2011 | Dussarrat |
| 7,964,490 | B2 | 6/2011 | Clendenning et al. |
| 8,017,184 | B2 | 9/2011 | Millward et al. |
| 2003/0129308 | A1 | 7/2003 | Chen et al. |
| 2007/0054487 | A1 | 3/2007 | Ma et al. |
| 2007/0243325 | A1 * | 10/2007 | Sneh ............ 427/248.1 |
| 2010/0092667 | A1 | 4/2010 | Gordon et al. |
| 2011/0048954 | A1 | 3/2011 | Rod |
| 2011/0263100 | A1 | 10/2011 | Hunks et al. |

FOREIGN PATENT DOCUMENTS

EP         2330109        6/2011
WO   WO 2009/086263      7/2009

OTHER PUBLICATIONS

Ihara et al. "High polymerization of methyl methacrylate with organonickel/MMAO systems" Jo of Poly Sci Part A: Polymer chem. Nov. 27, 2000; p. 4765-4775.*

(Continued)

*Primary Examiner* — Mandy Louie
(74) *Attorney, Agent, or Firm* — Servilla Whitney LLC

(57) ABSTRACT

Provided are precursors and methods of using same to deposit film consisting essentially of nickel. Certain methods comprise providing a substrate surface; exposing the substrate surface to a vapor comprising a precursor having a structure represented, without limitation to specific orientation, by:

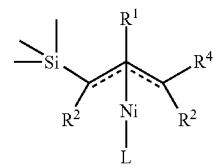

wherein $R^1$ and $R^2$ are each independently H or any C1-C3 alkyl group, $R^4$ is trimethylsilyl or C1-C3 alkyl, and L is any ligand that does not contain oxygen; and exposing the substrate to a reducing gas to provide a film consisting essentially of nickel on the substrate surface.

20 Claims, 4 Drawing Sheets

(56) References Cited

OTHER PUBLICATIONS

Quisenberry et al. "Trimethylsilylated allyl complexes of nickel. The stabilized bis(pi-allyl)nickel complex [eta3-1,3-(SiMe3)2C3H3]2Ni and its mono(pi-ally1)NiX (X=Br, I) derivatives" JACS, Mar. 3, 2005; p. 4376-4387.*
Benn, Reinhard et al., "$^1$H NMR Structural Increments for Alkyl Substituted $\eta^3$-Allyl Transition Metal Complexes", *Organic Magnetic Resonance*, vol. 14, No. 6 1980, 435-438.
Bunel, Emillo E. et al., "Pentamethylcyclopentadlenyl Acetylacetonate Complexes of Iron(II), Cobalt(II), and Nickel(II), Convenient Synthetic Entries to Mono-$\eta^5$-$C_5Me_5$ Derivatives", *Organometallics*, vol. 4, No. 9 1985, 1680-1682.
Fraenkel, Gideon et al., "Dynamics of Solvated Li$^+$ within exo,exo-[1,3- Bis(trimethylsilyl)allyl]lithium N,N,N',N'-Tetramethylethylenediamine Complex", *J. Am. Chem, Soc*, 112 1990, 1382-1286.
Ishikawa, Masato et al., "Ni Precursor for Chemical Vapor Deposition of NiSi", *Japanese Journal of Applied Physics*, vol. 43, No. 4B 2004, 1833-1836.
Ito, Yoshihiko et al., "Reaction of Ketone Enolates with Copper Dichloride. A Synthesis of 1,4-Diketones", *Journal of the American Chemical Society*, 07:10 May 14, 1975, 2912-2914.
Jones, R. A. et al., "The Influence of Steric Hindrance Upon the H-Bonded Association of Pyrroles with Pyridines", *TETRA*, vol. 35, No. 5-I 1979, 687-689.
Kada, T. et al., "Volatile CVD precursor for Ni film: cyclopentadienylallylnickel", *Journal of Crystal Growth* 275. 2005, e1115-e1119.
Kang, Jin-Kyu et al., "Metalorganic chemical vapor deposition of nickel films from Ni($C_5H_5$)$_2$/$H_2$", *J. Mater. Res.*, vol. 15, No. 8 Aug. 2000, 1828-1833.
Kuhn, Von Norbert et al., "2,5-Di-tert. butyl-3,4-dimethylpyrrol", *Chemiker-Zeitung.*, 113, Nr. 9 1989, 289-290.
Kuhn, Norbert et al., "The electronic structure of 1,1'-diazametallocenes and the snythesis and crystal structure of 2,2',5,5'-tetra-tert-buty1-1,1'- diazanickelocene", *Jornal of Organometallic Chemistry*, 456 1993, 97-106.
Kuhn, Norbert et al., "Xvi. *(2,5-$C_4{}^tBu_2$RHN)M$Cl_3$ (M=Ti, Zr, Hf; R=H, SiMe$_3$)-Azacyclopentadienyl-Komplexe der Gruppe 4-Metalle", *Journal of Organometallic Chemistry*, 440 1992, 289-296.

Lehmkuhl, Herbert et al., "Reaktionen von Nickelocen mit Organomagnesiumverbindungen und Bildung von $\eta\text{-}^3$-Allyl-$\eta^5$-cyclopentadienylnickel-Komplexen", *Liebigs Ann. Chem.* 1980, 744-753.
Quisenberry, Keith T. et al., "Trimethylsilylated Allyl Complexes of Nickel. The Stabilized Bis(Π-allyl)nickel Complex [$\eta^3$-1,3-(SiMe$_3$)$_2$C$_3$H$_3$]$_2$Ni and Its Mono(Π-allyl)NiX (X=Br, 1) Derivatives", *J. Am. Chem. Soc*, 127 2005, 4376-4387.
Schumann, Herbert et al., "Metallorganische Verbindunger der Lanthanoide XCVII Synthese und Strukturaufklarung von Dichloro($\eta^5$-2,5-di-ters.- butylpyrrolyl)bis(tetrahydrofuran) ytterbium(III)", *Journal of Organometallic Chemistry* 495 1995, C12-C14.
Smith, Michael E., et al., Me$_5$C$_5$Ni(acac): A Monomeric, Paramagnetic,18-Electron, Spin-Equilibrium Molecule, *J. Am. Cham. Soc*, 118, 1996, 11119-11128.
Uyanik, Muhammet et al., "2-Lodoxybenzenesultonic Acid as an Extremely Active Catalyst for the Selective Oxidation of Alchols to Aldehydes, Ketones, Carboxylic Acids, and Enones with Oxone", *J. Am. Chem. Soc.*, 131 2009, 251-262.
Westerhausen, Matthias et al., "Coordination Modes of 2,5-Di(tertbutyl)pyrrolids-Crystal Structures of HPyr*, Pyr*H thf, (thf)$_2$LiPyr*, and [(Me$_3$Si)$_3$C-Zn]$_2$(μ-Cl)(μ-Pyr*)(Pyr*=2,5-tBu$_2$NC$_4$H$_2$)", *Eur. J. Inorg. Chem.* 1998, 1175-1182.
Wilke, G. Article English Machine Translation, 2 pgs.
Wilke, G. et al., "Bis-m-allyl-nickle", *Angew. Chem.*, No. 23 1961, p. 756.
PCT International Search Report and Written Opinion in PCT/US2013/051094, mailed Oct. 16, 2013, 14 pgs.
PCT International Search Report and Written Opinion in PCT/US2013/051651, dated Nov. 25, 2013, 12 pgs.
Lehmkuhl, Herbert et al., "Alkinkomplexe des n-5-Cyclopentadienylnickelmethyls und deren Thermolyse", *Journal of Organometallic Chemistry*, 363 1989, 387-391.
Pasynkiewicz, S. et al., "Reactions of unstable compound {CpNiCH3} with acetylenes", *Journal of Organometallic Chemistry*, 429 1992, 135-141.
PCT International Preliminary Report on Patentability in PCT/US2013/051094, mailed Feb. 5, 2015, 7 pages.
PCT International Preliminary Report on Patentability in PCT/US2013/051651, mailed Feb. 5, 2015, 8 pages.

* cited by examiner

METHODS FOR PRODUCING NICKEL-CONTAINING FILMS

TECHNICAL FIELD

The present invention relates generally to methods of depositing thin films of metal. In particular, the invention relates to the use of coordination complexes containing nickel to deposit films consisting essentially of nickel.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures. One method for deposition of thin films is chemical vapor deposition (CVD). In this process, a wafer is typically exposed to one or more volatile precursors, which react to deposit films. A related process is atomic layer deposition (ALD), which employs sequential surface reactions to form layers of precise thickness controlled at the Angstrom or monolayer level. Most ALD processes are based on binary reaction sequences which deposit a binary compound film. Because the surface reactions are sequential, the two gas phase reactants are not in contact, and possible gas phase reactions that may form and deposit particles are limited.

There is a need for new deposition chemistries that are commercially viable, particularly in the area of elemental metal films, including nickel films for nickel silicide contacts. For example, nickel films have been deposited using $Ni(PF_3)_4$ and bis(cyclopentadienyl)Ni coordination complexes. However, each of these complexes has presented problems. $Ni(PF_3)_4$ and $Ni(CO)_4$ are toxic and bis(cyclopentadienyl)Ni can lead to carbon contamination in the film. Bis(allyl)nickel compounds are both more volatile and more reactive than the well-studied bis(cyclopentadienyl) nickel analogs, which has the potential to facilitate the metal film formation. However, bis(allyl) nickel compounds are generally too unstable for storage or clean incorporation into a deposition process. The present invention addresses these problems by providing novel chemistries.

SUMMARY

One aspect of the invention relates to a method of depositing a film consisting essentially of nickel. The method comprises providing a substrate surface; exposing the substrate surface to a precursor having a structure represented, without limitation to specific orientation, by:

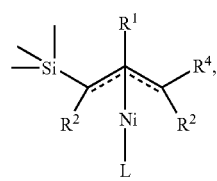

wherein $R^1$ and $R^2$ are each independently H or any C1-C3 alkyl group, $R^4$ is trimethylsilyl or C1-C3 alkyl, and L is any ligand that does not contain oxygen; and exposing the substrate to a reducing gas to provide a film consisting essentially of nickel on the substrate surface. It will be understood that the embodiments listed below may be combined not only as listed below, but in other suitable combinations in accordance with the scope of the invention.

In one or more embodiments, the precursor has a structure represented by:

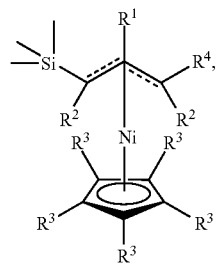

wherein $R^1$ and $R^2$ are each independently H or any C1-C3 alkyl group, $R^4$ is trimethylsilyl or C1-C3 alkyl, and each $R^3$ is independently H or methyl. In further embodiment, the precursor has a structure represented by:

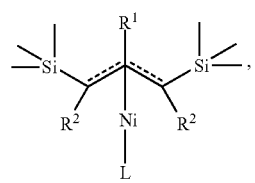

wherein $R^1$ and $R^2$ are each independently H or any C1-C3 alkyl group, and L is any ligand that does not contain oxygen. In yet further embodiments, the precursor has a structure represented by:

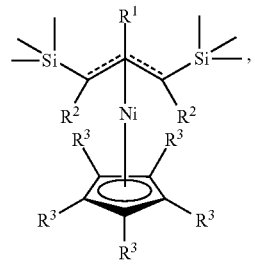

wherein $R^1$ and $R^2$ are each independently H or any C1-C3 alkyl group, and each $R^3$ is independently H or methyl. In one or more embodiments, the precursor has a structure represented by:

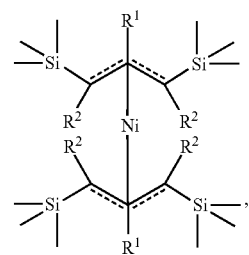

wherein $R^1$ and $R^2$ are each independently H or any C1-C3 alkyl group. In some embodiments, the precursor is homoleptic.

There are also variants in the process conditions. For example, in one or more embodiments, the substrate surface is exposed to the precursor and reductant gas substantially simultaneously or sequentially. In some embodiments, the reducing gas comprises ammonia gas or hydrogen gas. In one or more embodiments, the substrate surface contains a hydrogen-terminated surface.

One or more embodiments of the films provided herein exhibit reduced contamination. Thus, for example, in one or more embodiments, the film consisting essentially of nickel is oxide-free. In some embodiments, the film consisting essentially of nickel contains less than about 5% carbon.

A second aspect of the invention relates to a method of depositing a film consisting essentially of nickel, the method comprising: providing a substrate surface; substantially simultaneously or sequentially exposing the substrate surface to a precursor having a structure represented by:

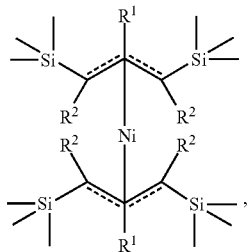

wherein $R^1$ and $R^2$ are each independently H or any C1-C3 alkyl group; and exposing the substrate to a reducing gas to provide a film consisting essentially of nickel on the substrate, wherein the film consisting essentially of nickel contains less than about 5% carbon. Any of the precursor and/or process embodiments described above may be used in this aspect, as appropriate. For example, in one or more embodiments, the precursor is homoleptic. In some embodiments, the reducing gas comprises ammonia gas or hydrogen gas. In one or more embodiments, the substrate surface contains a hydrogen-terminated surface. In some embodiments, the film consisting essentially of nickel is oxide-free.

Another aspect of the invention relates to a method of depositing a film consisting essentially of nickel, the method comprising: providing a substrate surface; substantially simultaneously or sequentially exposing the substrate surface to a precursor having a structure represented by:

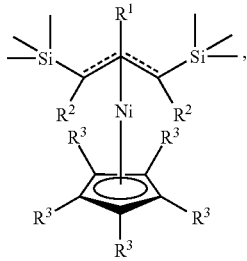

wherein $R^1$ and $R^2$ are each independently H or any C1-C3 alkyl group, and each $R^3$ is independently H or methyl; and exposing the substrate to a reducing gas to provide a film consisting essentially of nickel on the substrate, wherein the film consisting essentially of nickel contains less than about 5% carbon. Any of the appropriate embodiments described above may be applied in this aspect. Thus, for example, in one or more embodiments, the reducing gas comprises ammonia gas or hydrogen gas. In some embodiment, the substrate surface contains a hydrogen-terminated surface. In one or more embodiment, the film consisting essentially of nickel is oxide-free.

DETAILED DESCRIPTION

Figure 1:
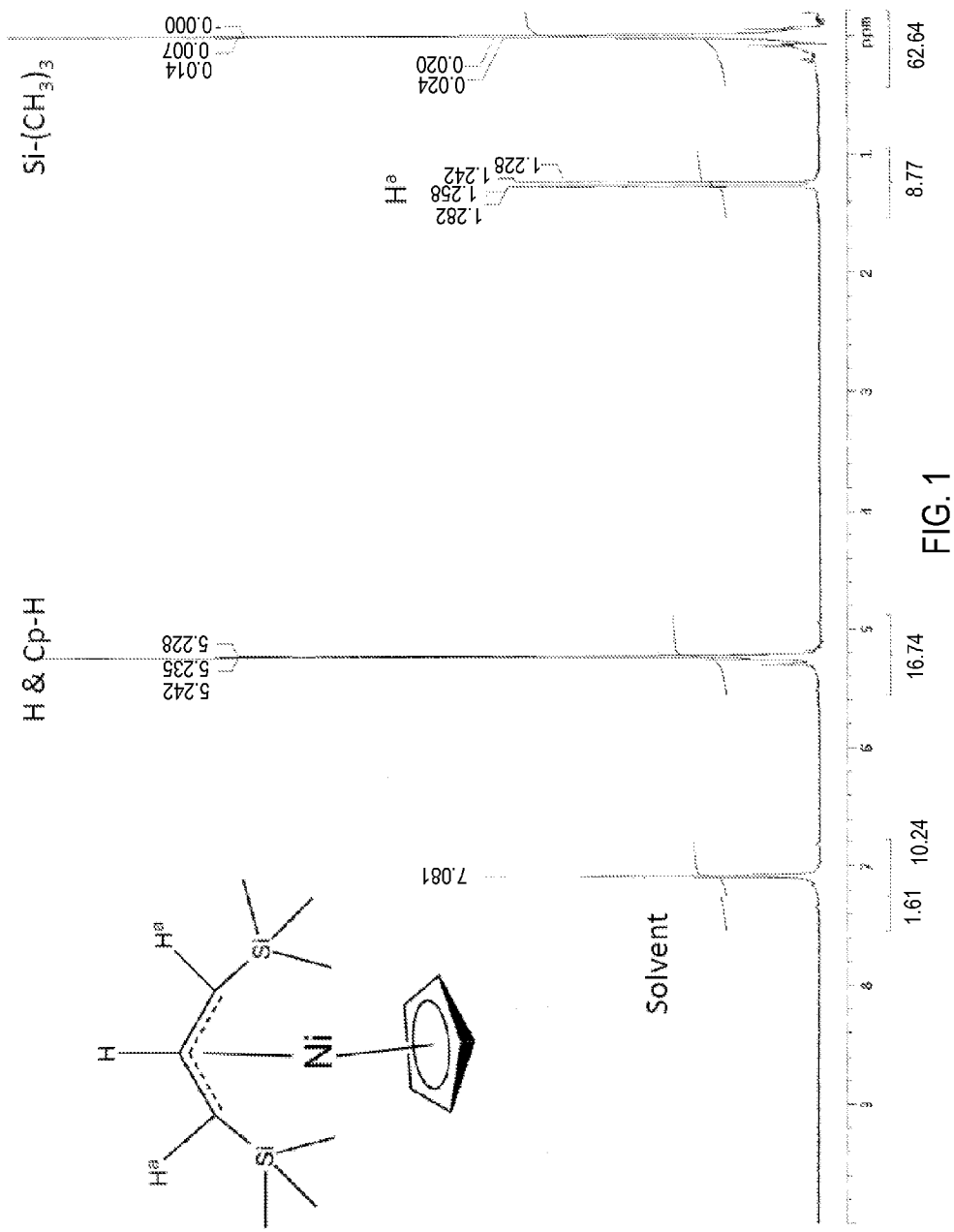
FIG. 1 shows the nuclear magnetic resonance (NMR) spectrum of a metal coordination complex according to one or more embodiments of the invention.

Before describing several exemplary embodiments of the invention, it is to be understood that the invention is not limited to the details of construction or process steps set forth in the following description. The invention is capable of other embodiments and of being practiced or being carried out in various ways. It is also to be understood that the complexes and ligands of the present invention may be illustrated herein using structural formulas which have a particular stereochemistry. These illustrations are intended as examples only and are not to be construed as limiting the disclosed structure to any particular stereochemistry. Rather, the illustrated structures are intended to encompass all such complexes and ligands having the indicated chemical formula.

As used herein, the term "consisting essentially of nickel" means that deposited layer contains mostly elemental nickel. In one or more embodiments, small amounts of impurities are within the meaning of the term. In one or more embodiments, the film contains no oxygen, and/or contains less than 5% carbon. In one or more further embodiments, the film contains less than about 3% or about 1% carbon.

The term "metal coordination complex" as used herein is used interchangeably with "metal complex" and "coordination complex," and includes structures that consist of a central metal atom bonded to one or more ligands. As will be discussed in more detail below, the metal complexes of the invention comprise of allyl-based ligands coordinated to nickel atoms.

It should be noted that all of the chemical structures shown herein are without limitation to specific orientation.

One aspect of the invention relates to such a metal coordination complex. The metal coordination complex has a structure represented by formula (I):

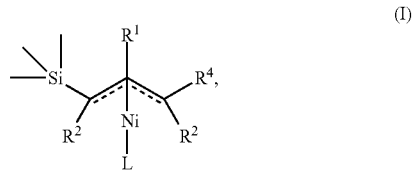

wherein R¹ and R² are each independently H or any C1-C3 alkyl group, R⁴ is trimethylsilyl or C1-C3 alkyl, and L is any ligand that does not contain oxygen. As stated above, formula (I) is shown without limitation to specific orientation. Thus, for example, the above formula covers embodiments where R⁴ is hydrogen and R² is methyl, as well as the reverse (i.e., where the silyl group and R⁴ are switched).

There are many suitable variants of precursor of formula (I). For example, in one or more embodiments, R⁴ is trimethylsilyl, resulting in a complex with at least one 1,1'-bis(trimethylsilyl)allyl ligand. Such a precursor may be represented by formula (II):

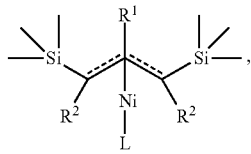
(II)

wherein R¹ and R² are each independently H or any C1-C3 alkyl group, and L is any ligand that does not contain oxygen.

There are also many variants in what the second ligand, L, may be selected as. In some embodiments, L is chosen such that the coordination complex is homoleptic. In some other embodiments, L is a cyclopentadienyl (Cp) or 1,2,3,4,5-pentamethylcyclopentadienyl (Cp*) ligand. Accordingly, in one or more embodiments, the precursor has a structure represented by formula (III):

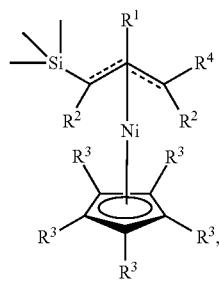
(III)

wherein R¹ and R² are each independently H or any C1-C3 alkyl group, R⁴ is trimethylsilyl or C1-C3 alkyl, and each R³ is independently H or methyl. In further embodiments, the precursor has a structure represented by formula (IV):

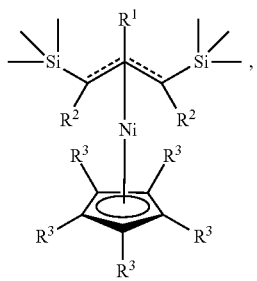
(IV)

wherein R¹ and R² are each independently H or any C1-C3 alkyl group, and each R³ is independently H or methyl.

In one or more embodiments, L may comprise a second trimethylsilyl allyl ligand. Thus, for example, the precursor may comprise two 1,1'-bis(trimethylsilyl)allyl ligands, as shown in formula (V):

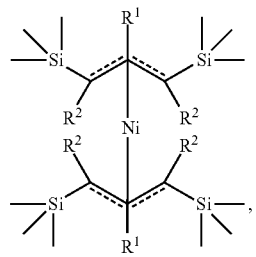
(V)

wherein R¹ and R² are each independently H or any C1-C3 alkyl group.

The precursors described herein are alternatives to previously used precursors like Ni(PF₃)₄ and metallocene-based precursors, such as bis(cyclopentadienyl)nickel. The precursors according to formula (I) above are lower toxicity, but cost competitive as compared to Ni(PF₃)₄. The precursors are also likely to results in less carbon contamination than previously used bis(cyclopentadienyl)nickel complexes.

The synthesis of this metal coordination complex begins with the production of the trimethylsilyl allyl-based ligand according to known methods in the art. For example, in embodiments relating to 1,1'-bis(trimethylsilyl)allyl ligand, that ligand is first synthesized according to known methods (See i.e., Fraenkel, Dynamics of Solvated Li+ within exo,exo-[1,3-Bis(trimethylsilyl)allyl]lithium N,N,N',N'-Tetramethylenediamine Complex (1990)). Then, the allene is metalated with butyllithium, and then reacted with nickel halide ether complex to form the bis(pi-allyl)nickel complex (See i.e., Quisenberry, et al., Trimethylsilylated Allyl Complexes of Nickel (2004)).

The properties of a specific metal coordination complex for use in the ALD deposition methods of the invention can be evaluated using methods known in the art, allowing selection of appropriate temperature and pressure for the reaction. In general, lower molecular weight and the presence of functional groups result in a melting point that yields liquids at typical delivery temperatures and increased vapor pressure.

In one or more embodiments, these metal coordination complexes are useful to deposit thin films consisting essentially of nickel. Thus, another aspect of the invention relates to a method of depositing a film consisting essentially of nickel. The method comprises providing a substrate surface; exposing the substrate surface to a precursor having a structure represented, by formula (I):

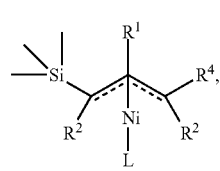
(I)

wherein R¹ and R² are each independently H or any C1-C3 alkyl group, R⁴ is trimethylsilyl or C1-C3 alkyl, and L is any ligand that does not contain oxygen; and exposing the substrate to a reducing gas to provide a film consisting essentially of nickel on the substrate surface. It should be noted that the above structure is representative without limitation to specific orientation.

In one or more embodiments, the substrate surface is exposed to the precursor and reductant gas substantially simultaneously or sequentially. As used herein, "substantially simultaneously" refers to either co-flow or where there is merely overlap between exposures of the precursor and reductant. The reducing gas may comprise ammonia or hydrogen gas.

In one or more embodiments, the films deposited via the methods described herein are suitable for use in the production of low-resistance, nickel silicide contacts because of reduced levels of carbon and/or oxygen contaminants. Once the nickel film is deposited over a silicon substrate, it can be converted to the silicide form by reaction with a silicon substrate. In one or more embodiments, this may be achieved through annealing at slightly elevated temperatures, if necessary. However, in one or more embodiments, the temperature does not exceed about 250 to about 275° C., because of the possibility of the formation of the disilicide ($NiSi_2$), which is too electrically resistive. In other embodiments, such as those relating to anti-corrosion coatings, there would not necessarily be this temperature limit.

While not wishing to be bound to any particular theory, it is thought that when the substrate is exposed to the complex, the complex chemically decomposes the nickel into the film and produce vapor-phase ligands (or vapor-phase ligand decomposition products). Decomposition is achieved by contacting the metal complex with a reducing gas results in an exchange reaction between the metal coordination complex, or the surface-bound ligands, and the reducing gas, thereby dissociating the bound metal complex and producing a first layer consisting essentially of nickel on the surface of the substrate. The neutral ligands or ligand decomposition products can then be removed, and not incorporated into the film.

The substrate for deposition of the elemental thin layer films may be any substrate suitable for conformal film coating in an ALD or CVD process. Such substrates include silicon, silica or coated silicon, metal, metal oxide and metal nitride. In one aspect of the invention, the substrate is a semiconductor substrate. In one or more embodiments, the substrate surface may comprise a hydrogen-terminated surface.

In one or more embodiments, exposure of the substrate surface to the vapor comprising the precursor and the reducing gas occurs under an oxide-free environment. In further embodiments, the deposited film contains no oxygen incorporation (i.e., is oxide-free). Oxide-free films are achievable using the precursors and methods described herein because the ligands do not contain oxygen atoms.

The above metal coordination complexes can be used in ALD or CVD processes to deposit the films described herein. As used herein, the phrase "atomic layer deposition" is used interchangeably with "ALD," and refers to a process which involves sequential exposures of chemical reactants, and each reactant is deposited from the other separated in time and space. However, according to one or more embodiments, the phrase "atomic layer deposition" is not necessarily limited to reactions in which each reactant layer deposited is limited to a monolayer (i.e., a layer that is one reactant molecule thick). Atomic layer deposition is distinguished from "chemical vapor deposition" or "CVD," in that CVD refers to a process in which one or more reactants continuously form a film on a substrate by reaction in a process chamber containing the substrate or on the surface of the substrate.

The specific precursor may be selected according to any of the embodiments listed above. Thus for example, in one embodiment, the method comprises providing a substrate surface; substantially simultaneously or sequentially exposing the substrate surface to a precursor having a structure represented by formula (V):

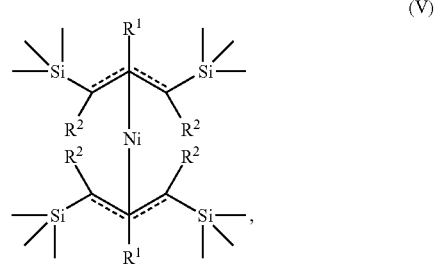

wherein $R^1$ and $R^2$ are each independently H or any C1-C3 alkyl group; and exposing the substrate to a reducing gas to provide a film consisting essentially of nickel on the substrate, wherein the film consisting essentially of nickel contains less than about 5% carbon. Any of the process variants described herein may be used in this embodiment.

In another embodiment, the method comprises providing a substrate surface; substantially simultaneously or sequentially exposing the substrate surface to a precursor having a structure represented by:

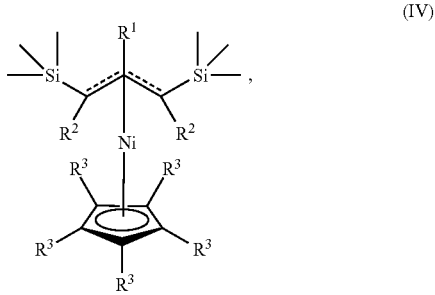

wherein $R^1$ and $R^2$ are each independently H or any C1-C3 alkyl group, and each $R^3$ is independently H or methyl; and exposing the substrate to a reducing gas to provide a film consisting essentially of nickel on the substrate, wherein the film consisting essentially of nickel contains less than about 5% carbon. Again, any of the process variants described herein may be used in this embodiment.

Optionally, a second atomic layer may be formed added on the first layer by repeating any of the process reaction cycles described above. Any hydrogen remaining from the preceding reduction reaction may be purged from the deposition chamber using an inert gas. A metal coordination complex in vapor phase is again flowed into the chamber/exposed to metal film on the substrate surface. An exchange reaction occurs between the metal coordination complex in the vapor phase and hydrogen atoms on the metal of the first layer. This displaces one of the ligands from the vapor phase metal coordination complex and leaves the metal atom of the metal coordination complex bound to the metal atom of the first layer. The reaction time, temperature and pressure are selected to create a metal-surface interaction and form a layer on the surface of the substrate. Unreacted vapor phase metal coordination complex and released ligand can then be purged from the deposition chamber using an inert gas. A reducing gas may again be flowed into the deposition chamber to reduce the bond(s) between the metal and any remaining ligand(s), releasing the remaining ligand(s) from the metal center and producing a second layer on the first layer.

Additional repetitions of the deposition cycle may be used to build a layer of elemental metal of the desired thickness.

In one or more embodiments, the substrate surface has a temperature of greater than about 70, 80, 90 or 100° C. and less than about 250, 225, 200 or 175° C. While not wishing to be bound to any particular theory, it is thought that low temperatures at which the process is able to be carried out prevents carbon incorporation.

The deposition can be carried out at atmospheric pressure but is more commonly carried out at a reduced pressure. The vapor pressure of the metal coordination complex should be low enough to be practical in such applications.

In some embodiments, one or more layers may be formed during a plasma enhanced atomic layer deposition (PEALD) process. In some processes, the use of plasma provides sufficient energy to promote a species into the excited state where surface reactions become favorable and likely. Introducing the plasma into the process can be continuous or pulsed. In some embodiments, sequential pulses of precursors (or reactive gases) and plasma are used to process a layer. In some embodiments, the reagents may be ionized either locally (i.e., within the processing area) or remotely (i.e., outside the processing area). In some embodiments, remote ionization can occur upstream of the deposition chamber such that ions or other energetic or light emitting species are not in direct contact with the depositing film. In some PEALD processes, the plasma is generated external from the processing chamber, such as by a remote plasma generator system. The plasma may be generated via any suitable plasma generation process or technique known to those skilled in the art. For example, plasma may be generated by one or more of a microwave (MW) frequency generator or a radio frequency (RF) generator. The frequency of the plasma may be tuned depending on the specific reactive species being used. Suitable frequencies include, but are not limited to, 2 MHz, 13.56 MHz, 40 MHz, 60 MHz and 100 MHz. Although plasmas may be used during the deposition processes disclosed herein, it should be noted that plasmas may not required. Indeed, other embodiments relate to deposition processes under very mild conditions without a plasma.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or it can be moved from the first chamber to one or more transfer chambers, and then moved to the desired separate processing chamber. Accordingly, the processing apparatus may comprise multiple chambers in communication with a transfer station. An apparatus of this sort may be referred to as a "cluster tool" or "clustered system", and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present invention are the Centura® and the Endura®, both available from Applied Materials, Inc., of Santa Clara, Calif. The details of one such staged-vacuum substrate processing apparatus is disclosed in U.S. Pat. No. 5,186,718, entitled "Staged-Vacuum Wafer Processing Apparatus and Method," Tepman et al., issued on Feb. 16, 1993. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, preclean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants after forming the silicon layer on the surface of the substrate.

As discussed above, in some embodiments, the deposited films are oxide-free. In further embodiments, deposition occurs without a break in vacuum and/or without exposure to ambient conditions, thereby preventing exposure (and thus incorporation) of oxygen.

According to one or more embodiments, a purge gas is injected at the exit of the deposition chamber to prevent reactants from moving from the deposition chamber to the transfer chamber and/or additional processing chamber. Thus, the flow of inert gas forms a curtain at the exit of the chamber.

The substrate can be processed in single substrate deposition chambers, where a single substrate is loaded, processed and unloaded before another substrate is processed. The substrate can also be processed in a continuous manner, like a conveyer system, in which multiple substrate are individually loaded into a first part of the chamber, move through the chamber and are unloaded from a second part of the chamber. The shape of the chamber and associated conveyer system can form a straight path or curved path. Additionally, the processing chamber may be a carousel in which multiple substrates are moved about a central axis and are exposed to deposition, etch, annealing, cleaning, etc. processes throughout the carousel path.

During processing, the substrate can be heated or cooled. Such heating or cooling can be accomplished by any suitable means including, but not limited to, changing the temperature of the substrate support and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discrete steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

EXAMPLES

Example 1

A nickel metal coordination complex with one Cp ligand and one 1,1'-bis(trimethylsilyl)allyl ligand was produced and analyzed using HNMR. This would correspond to formula (IV) above, where $R^1$, $R^2$ and $R^3$ are all hydrogen. The hydrogens have been labeled as shown in FIG. 1.

FIG. 1 also shows the resulting NMR spectra. There are four sets of peaks shown. The first at around 7.1 ppm relates to the solvent. The next at around 5.2 ppm relates to the Cp hydrogens and the hydrogen atom of the central carbon atom in the allyl ligand. The peak at around 1.2 ppm relates to "$H^a$," the hydrogen atoms of each of the terminal carbons in allyl ligand. The final set of peaks at around 0 ppm relates to the hydrogens from the six trimethylsilyl groups.

Example 2

Figure 2:
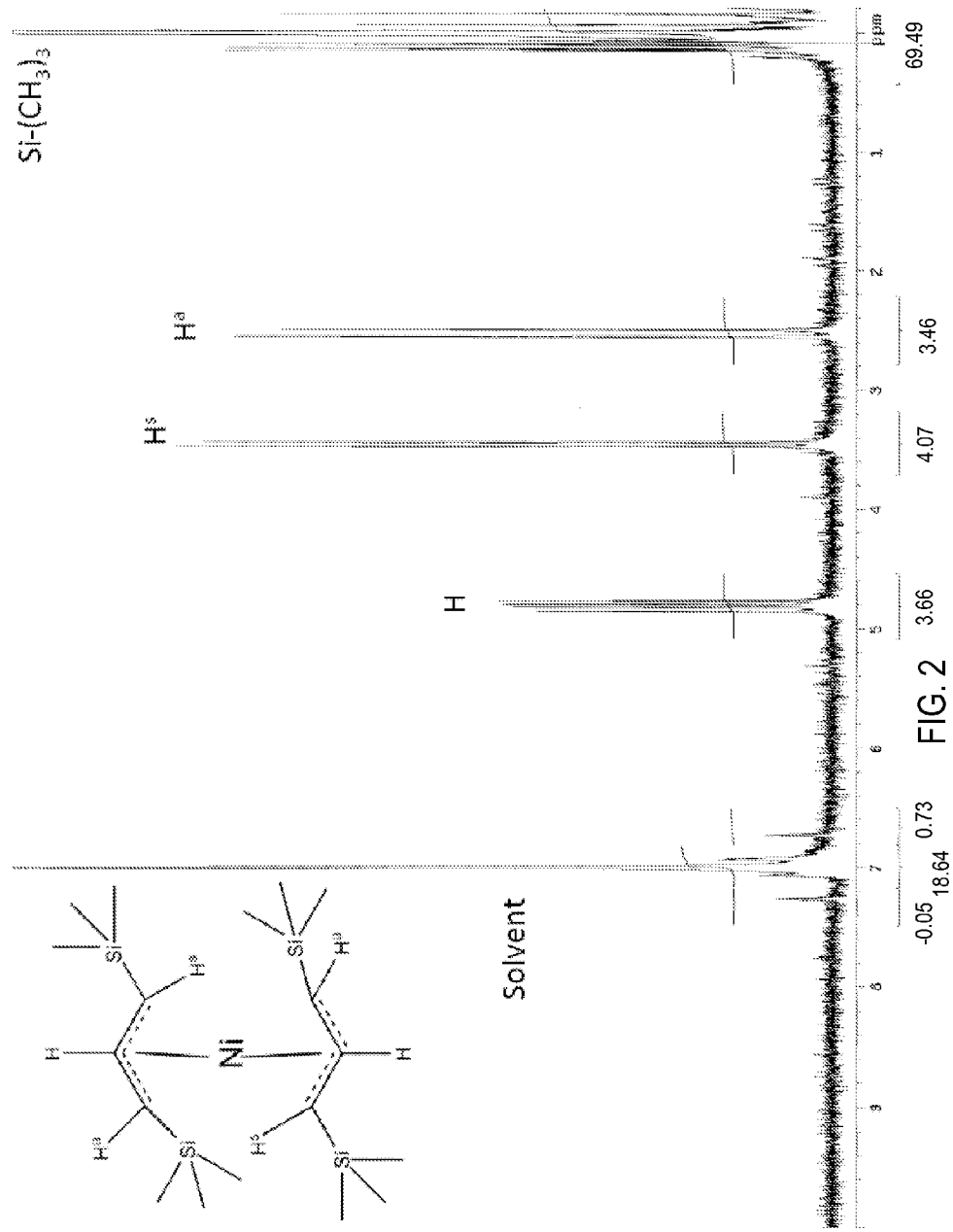
FIG. 2 shows the nuclear magnetic resonance (NMR) spectrum of a metal coordination complex according to one or more embodiments of the invention.

A nickel metal coordination complex with two 1,1'-bis(trimethylsilyl)allyl ligands was produced and analyzed using HNMR. This would correspond to formula (V) above, where $R^1$ and $R^2$ are all hydrogen. The hydrogens have been labeled as shown in FIG. 2. It should be noted that there is some peak splitting due to the presence of a diastereomer mixture.

FIG. 2 shows the resulting NMR spectra. There are five sets of peaks shown. The first at around 7.0 ppm relates to the solvent. The next at around 4.8 ppm relates to the hydrogen atom of the central carbon atom in the allyl ligand. The peak at around 3.4 ppm relates to "$H^s$," the hydrogen atom of one of the terminal carbons in allyl ligand, with the next peak around 2.5 ppm relating to "$H^a$," the hydrogen of the other terminal carbon in the allyl ligand. The final set of peaks at around 0 ppm relates to the hydrogens from the six trimethylsilyl groups.

Example 3

Figure 3:
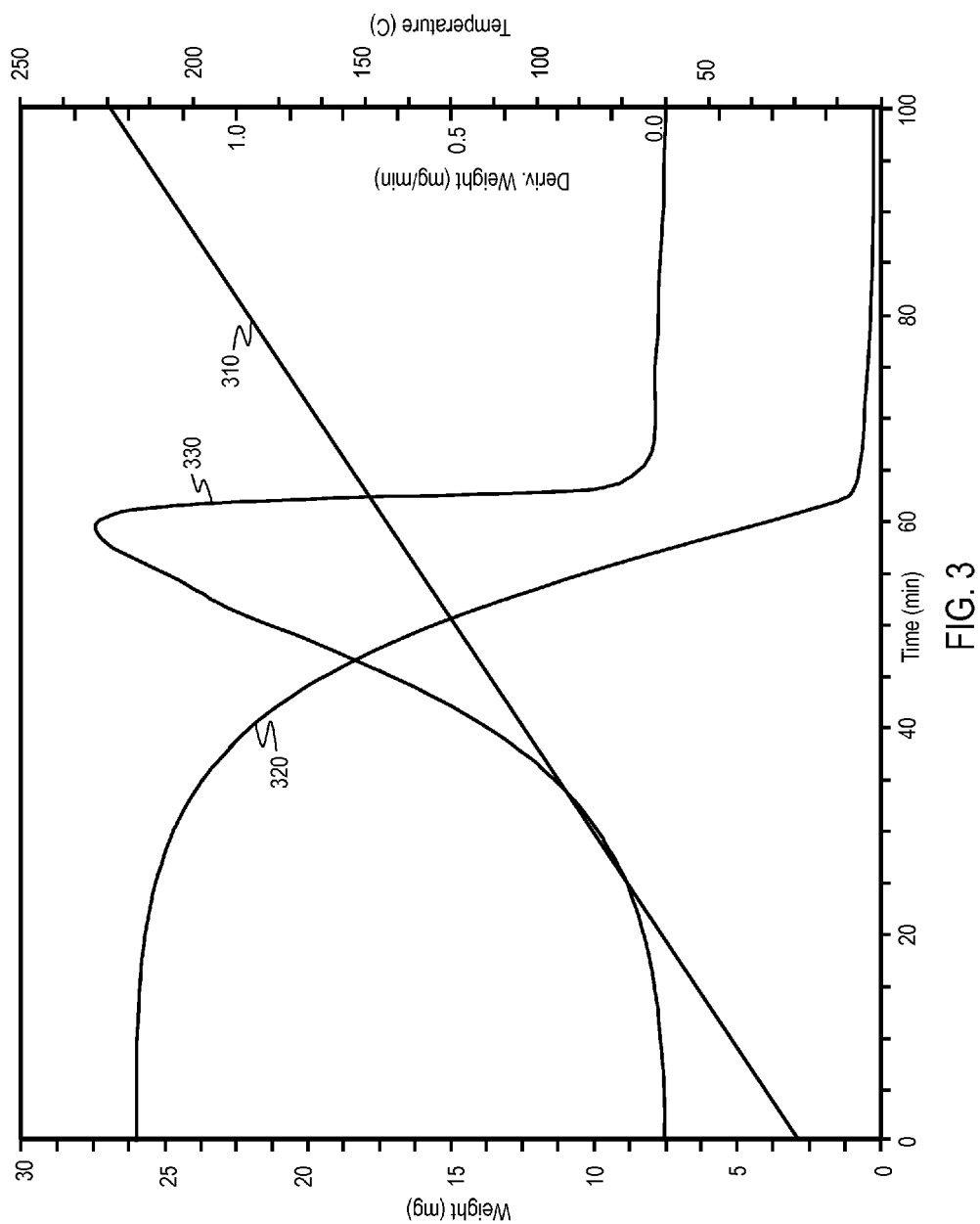
FIG. 3 shows a thermogravimetric analysis of a metal coordination complex according to one or more embodiments of the invention.

FIG. 3 shows the thermogravimetric analysis of the coordination complex from Example 1. The figure is a representation wherein any noise has been smoothed out. The weight of the sample material for each complex was measured as the material was exposed to increasing temperature. As the temperature is increased (shown by temperature ramping 310), the complexes evaporate, which decreases the measured weight. FIG. 3 shows both the weight of the material 320 as a function of time as well as the first derivative of the weight 330.

As can be seen from the data, the complex material decreased simply with increasing temperature, indicating that with increasing temperature, the complex evaporated. Indeed, the weight of the material 320 approaches zero, indicated that the material evaporated as opposed to decomposed.

This relatively simple vaporization of the complex demonstrates stability of the complex, in the absence of a reducing gas. It is thought that thermal instability, leading to non-volatile residue, contributes to contamination, particularly that of carbon, into the film.

Example 4

Figure 4:
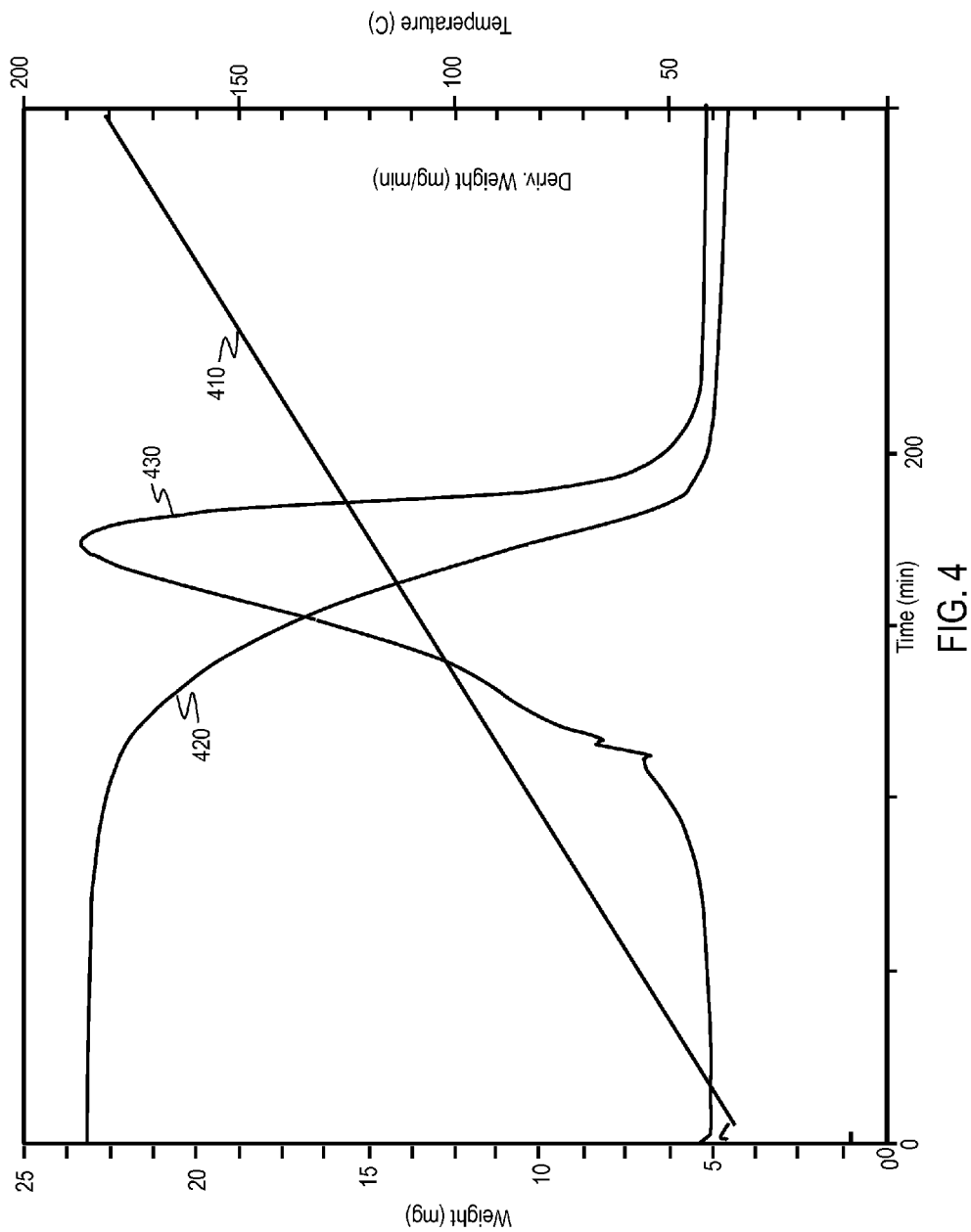
FIG. 4 shows a thermogravimetric analysis of a metal coordination complex according to one or more embodiments of the invention.

FIG. 4 shows the thermographic analysis of the coordination complex from Example 2. The figure is a representation wherein any noise has been smoothed out. The weight of the sample material for each complex was measured as the material was exposed to increasing temperature. As the temperature is increased (shown by temperature ramping 410), the complexes evaporate, which decreases the measured weight. FIG. 4 shows both the weight of the material 420 as a function of time as well as the first derivative of the weight 430.

As can be seen from the data, the complex material decreased simply with increasing temperature, indicating that with increasing temperature, the complex evaporated. The weight does not reach zero, indicating that there is some decomposition.

This relatively simple evaporation and decomposition of the complex demonstrates stability of the complex at elevated temperatures while demonstrating the thermal decomposition needed for CVD. It is thought that this type of instability contributes to contamination, particularly that of carbon, into the film. Taken in conjunction with Example 3, the thermogravimetric analysis proves the tunability of the nickel complex thermal decomposition temperature.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of depositing a film consisting essentially of nickel, the method comprising:
providing a substrate surface;
exposing the substrate surface to a precursor having a structure represented by:

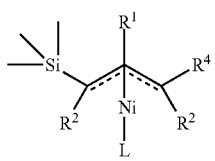

wherein R¹ and R² are each independently H or any C1-C3 alkyl group, R⁴ is trimethylsilyl or C1-C3 alkyl, and L is any ligand that does not contain oxygen; and exposing the substrate to a reducing gas to provide a film consisting essentially of nickel on the substrate surface.

2. The method of claim 1, wherein the precursor has a structure represented by:

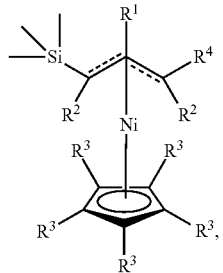

wherein R¹ and R² are each independently H or any C1-C3 alkyl group, R⁴ is trimethylsilyl or C1-C3 alkyl, and each R³ is independently H or methyl.

3. The method of claim 1, wherein the precursor has a structure represented by:

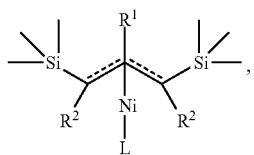

wherein R¹ and R² are each independently H or any C1-C3 alkyl group, and L is any ligand that does not contain oxygen.

4. The method of claim 3, wherein the precursor has a structure represented by:

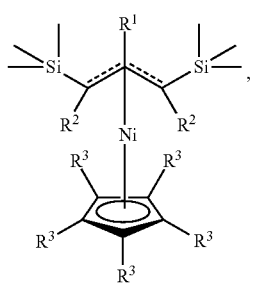

wherein R¹ and R² are each independently H or any C1-C3 alkyl group, and each R³ is independently H or methyl.

5. The method of claim 1, wherein the precursor has a structure represented by:

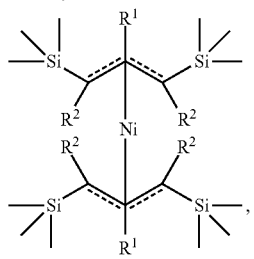

wherein R¹ and R² are each independently H or any C1-C3 alkyl group.

6. The method of claim 5, wherein the precursor is homoleptic.

7. The method of claim 1, wherein the substrate surface is exposed to the precursor and reductant gas substantially simultaneously or sequentially.

8. The method of claim 1, wherein the reducing gas comprises ammonia gas or hydrogen gas.

9. The method of claim 1, wherein the substrate surface contains a hydrogen-terminated surface.

10. The method of claim 1, wherein the film consisting essentially of nickel is oxide-free.

11. The method of claim 1, wherein the film consisting essentially of nickel contains less than about 5% carbon.

12. A method of depositing a film consisting essentially of nickel, the method comprising:
providing a substrate surface;
substantially simultaneously or sequentially exposing the substrate surface to a precursor having a structure represented by:

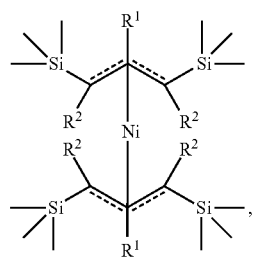

wherein R¹ and R² are each independently H or any C1-C3 alkyl group; and exposing the substrate to a reducing gas to provide a film consisting essentially of nickel on the substrate, wherein the film consisting essentially of nickel contains less than about 5% carbon.

13. The method of claim 12, wherein the precursor is homoleptic.

14. The method of claim 12, wherein the reducing gas comprises ammonia gas or hydrogen gas.

15. The method of claim 12, wherein the substrate surface contains a hydrogen-terminated surface.

16. The method of claim 12, wherein the film consisting essentially of nickel is oxide-free.

17. A method of depositing film consisting essentially of nickel, the method comprising:
providing a substrate surface;
substantially simultaneously or sequentially exposing the substrate surface to a precursor having a structure represented by:

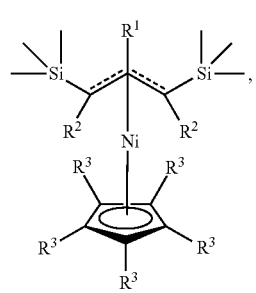

wherein $R^1$ and $R^2$ are each independently H or any C1-C3 alkyl group, and each $R^3$ is independently H or methyl; and exposing the substrate to a reducing gas to provide a film consisting essentially of nickel on the substrate, wherein the film consisting essentially of nickel contains less than about 5% carbon.

18. The method of claim 17, wherein the reducing gas comprises ammonia gas or hydrogen gas.

19. The method of claim 17, wherein the substrate surface contains a hydrogen-terminated surface.

20. The method of claim 17, wherein the film consisting essentially of nickel is oxide-free.

* * * * *